United States Patent
Lou et al.

(10) Patent No.: US 12,146,179 B2
(45) Date of Patent: Nov. 19, 2024

(54) METHOD FOR PRODUCING SPECIAL OIL OPO BY WAY OF MICROBIAL FERMENTATION

(71) Applicant: SOUTH CHINA UNIVERSITY OF TECHNOLOGY, Guangzhou (CN)

(72) Inventors: Wenyong Lou, Guangzhou (CN); Linshang Zhang, Guangzhou (CN); Minhua Zong, Guangzhou (CN); Zifu Ni, Guangzhou (CN); Jiguo Yang, Guangzhou (CN)

(73) Assignee: SOUTH CHINA UNIVERSITY OF TECHNOLOGY, Guangzhou (CN)

(*) Notice: Subject to any disclaimer, the term of this patent is extended or adjusted under 35 U.S.C. 154(b) by 456 days.

(21) Appl. No.: 17/614,331

(22) PCT Filed: Oct. 31, 2019

(86) PCT No.: PCT/CN2019/114911
§ 371 (c)(1),
(2) Date: Nov. 25, 2021

(87) PCT Pub. No.: WO2020/238010
PCT Pub. Date: Dec. 3, 2020

(65) Prior Publication Data
US 2022/0220518 A1    Jul. 14, 2022

(30) Foreign Application Priority Data
May 25, 2019 (CN) .......................... 201910442599.7

(51) Int. Cl.
*C12P 7/64*       (2022.01)
(52) U.S. Cl.
CPC ..................................... *C12P 7/64* (2013.01)
(58) Field of Classification Search
CPC ................................ C12P 7/64; C12P 7/6463
See application file for complete search history.

(56) References Cited

FOREIGN PATENT DOCUMENTS

| | | | |
|---|---|---|---|
| CN | 103305332 | 9/2013 | |
| CN | 104561145 | 4/2015 | |
| CN | 105219811 | 1/2016 | |
| CN | 105441492 | 3/2016 | |
| CN | 107473963 | 12/2017 | |
| CN | 108841880 A | * 11/2018 | ............ C12P 7/6454 |
| CN | 108913725 | 11/2018 | |
| CN | 109082447 | 12/2018 | |
| CN | 110184311 | 8/2019 | |

OTHER PUBLICATIONS

Xiang Li; et al., "Research progress on industrialized application of microbial oils," China Oils and Fats, vol. 35, No. 11, Nov. 2010, pp. 10-13.

Xiang, Guangming et al., "Research progress of microbial oil," Cereals and Oils Processing, Issue 9, Sep. 2008, pp. 1-5.

"International Search Report (Form PCT/ISA/210) of PCT/CN2019/114911," mailed on Feb. 6, 2020, with English translation thereof, pp. 1-4.

\* cited by examiner

*Primary Examiner* — Tekchand Saidha
(74) *Attorney, Agent, or Firm* — JCIPRNET

(57) ABSTRACT

Disclosed is a method for producing special oil OPO by way of microbial fermentation. The method comprises the following steps: inoculating microorganisms to an activating culture medium for shake cultivation treatment to obtain an activated culture; adding an organic matter into a minimal medium to obtain an optimized culture medium; inoculating the culture into the optimized culture medium for shake cultivation treatment to obtain a culture solution; carrying out centrifugal treatment on the culture solution, taking a precipitate, washing the precipitate and freeze-drying the precipitate, adding a hydrochloric acid solution to obtain a mixture; and adding an organic solvent into the mixture for extraction, and removing the solvent to obtain the OPO, wherein the microorganisms are *Rhodococcus opacus* PD630.

9 Claims, 3 Drawing Sheets

METHOD FOR PRODUCING SPECIAL OIL OPO BY WAY OF MICROBIAL FERMENTATION

CROSS-REFERENCE TO RELATED APPLICATION

This application is a 371 of international application of PCT application serial no. PCT/CN2019/114911, filed on Oct. 31, 2019, which claims the priority benefit of China application no. 201910442599.7, filed on May 25, 2019. The entirety of each of the above-mentioned patent applications is hereby incorporated by reference herein and made a part of this specification.

TECHNICAL FIELD

The present invention belongs to the field of microorganisms, and in particular relates to a method for producing special oil OPO by way of microbial fermentation.

BACKGROUND OF RELATED ART

An OPO structured lipid is a first-tier oil (a human milk substitute) of infant formula, and has the characteristics of being easily bonded with sodium cholate, easy to digest and absorb, free of high-melting-point soap, beneficial to absorb metal ions such as calcium and magnesium. Preparation methods of OPO include an enzyme method, a fractionation method and a chemical synthesis method. The enzyme method is primarily a method for preparing OPO-enriched oil by adding oleic acid or ethyl oleate or high olein for acidolysis or ester exchange by taking palm stearin as a primer by means of 1,3-site specific lipase. The enzyme method for preparing OPO is a mainstream method for industrial operation at present. However, the method is relatively high in cost, and the price of enzyme is high. In addition, the method further has a problem that a technical barrier of acyl migration cannot be overcome. CN109082447A discloses a process for preparing OPO by an enzyme method by taking high oleic acid peanut oil as a source of oleic acid. The process is featured in cancelling a step of oleic acid purification. Oleic acid or ethyl oleate prepared by hydrolysis or alcoholysis of peanut oil is directly reacted with palm stearin, and a reaction product is subjected to molecular distillation purification. The content of OPO produced by the method is 46.35-44.17%, which can completely meet the requirements of GB 30604-2015. CN105219811A discloses a method for preparing OPO by microwave assisted enzyme method acidolysis. The method is characterized in that a microwave technology is applied in a reaction, and meanwhile, 15% of algal oil is doped into raw materials, so that the produced OPO contains a small amount of DHA. CN108913725A discloses a method for preparing OPO by enzyme method acidolysis. The method is characterized in that an electron beam is irradiated and applied to an enzymatic reaction, a dosage of the enzymatic reaction is 20 Gy, irradiation is performed for 2 hours, and the yield of OPO treated by an enzymatic reaction system is increased by 61.25%.

The fractionation method is a method for enriching OPO by a fractionation technology by using OPO-containing natural oil (lard). The fractionation method is a pure physical operating process, and is minimum in health risk. However, the fractionation process is complex, high in technical difficulty and is high in safety risk by using a solvent. The raw materials are merely restricted to lard, cannot meet the requirements of religion and cannot be produced industrially on a large scale. CN103305332A discloses a method for fractionating and enriching OPO in lard by fractionation coupling solvent by a dry method. Finally, oil with the OPO content greater than 40% is obtained. A main process thereof includes: oil is smelted at 60° C., the temperature is decreased to 28° C. rapidly, then the temperature is decreased to 16° C. slowly and the temperature is maintained for 10 hours, then the mixture is filtered to obtain a liquid component and a solid component, the liquid component is mixed with acetone, the temperature is decreased to 5° C. from 40° C. rapidly and the temperature is maintained for 20 hours, where liquid oil obtained by vacuum suction filtration is high OPO oil.

The chemical synthesis method obtains high purity OPO easily. But it is hard to obtain food grade level raw materials, so that the chemical synthesis method can only be performed in a lab and cannot realize industrial production truly. CN107473963A discloses a process for preparing OPO by a two-step method by taking 1,3-dichloropropanol, methyl palmitate and sodium oleate. First, 1,3-dichloropropanol and methyl palmitate are heated and refluxed in an organic solvent to prepare 1,3-dichloro-2-octadecanoate. In a second step of the reaction, 1,3-dichloro-2-octadecanoate is reacted with sodium oleate for 2-5 hours at 50-100° C. under protection of nitrogen, and the purity of prepared OPO is 96%.

SUMMARY OF THE INVENTION

In order to overcome defects in the prior art, the objective of the present invention is to provide a method for producing special oil OPO by way of microbial fermentation. The method can obtain high purity OPO oil by performing fermentation, crushing and oil extraction only. The method is simple in process, low in cost and huge in industrial prospect.

The objective of the present invention is at least realized by one of the technical schemes as follows.

The present invention provides is a method for producing OPO by way of microbial fermentation of *Rhodococcus*. The *Rhodococcus* is specifically *Rhodococcus opacus* PD630. Production of OPO by fermentation includes the following steps: 1, performing culture activation; 2, performing cultivation in an MSM culture medium, where the MSM culture medium is an inorganic salt culture medium, and a carbon source contains oleate and palmitate of high content; 3, collecting cells after cultivation; and 4, crushing the cells, and extracting oil, where the obtained oil is oil rich in OPO.

A method for producing special oil OPO by way of microbial fermentation provided by the present invention includes the following steps:

(1) Culture activation

Inoculating microorganisms to an activating culture medium, and carrying out a shake cultivation treatment to obtain an activated culture;

(2) Preparation of an optimized culture medium

Adding an organic matter into a minimal medium, uniformly mixing, and carrying out a sterilizing treatment to obtain an optimized culture medium;

(3) Inoculating the activated culture in the step (1) into the optimized culture medium in the step (2) and carrying out the shake cultivation treatment to obtain a culture solution;

(4) Carrying out a centrifugal treatment on the culture solution in the step (3), taking a precipitate, washing the precipitate and freezing and drying the precipitate to obtain a freeze-dried powder, and adding a hydrochloric acid solution to obtain a mixture; and (5) Adding an organic solvent into the mixture in the step (4), carrying out an extraction treatment, and removing the solvent to obtain an oil mixture, where the oil mixture contains the special oil OPO.

Further, the culture in the step (1) includes *Rhodococcus opacus* PD630, and the activating culture medium comprises a bouillon culture-medium and an LB culture medium.

Further, the microorganism in the step (1) includes *Rhodococcus opacus* PD630. A temperature for shake cultivation treatment ranges from 20 degrees centigrade to 40 degrees centigrade, a rotating speed for shake cultivation treatment ranges from 80 rpm to 250 rpm, the rotating speed is further optimized to 120-200 rpm, and is further optimized again to 150-180 rpm; a time for shake cultivation treatment ranges from 12 hours to 60 hours, and the time is further optimized to 18-48 hours and is further optimized again to 20-36 hours.

Further, the organic matter in the step (2) includes palmitic acid, oleic acid, palmitate, oleate, cetane, octodecane, palm oil, a fractionated product of palm oil, high oleic acid triglyceride and a mixture of these organic matters; and an additive amount of the organic matter is 0.1-10% (w/w) of the minimal medium by mass, and the additive amount is further optimized to 0.3-7% and is further optimized to 0.5-4% again.

Further, a way of sterilizing treatment in the step (2) includes high-temperature and high-pressure sterilization (121 degrees centigrade, 20 minutes) and medium and low-pressure sterilization (115 degrees centigrade, 15 minutes).

Further, the minimum medium in the step (2) can be the MSM culture medium, and the carbon source in the culture medium contains palmitic acid and oleic acid of high proportion, or palmitate and oleate of high proportion, or hexadecane and oleic acid and oleate of high proportion, where a proportion (mass ratio) of palmityl to oleoyl is 1:1.4 to 1:3.

Further, an inoculum size of the inoculating in the step (3) is 0.1-10% (v/v) of the optimized culture medium by volume, and the inoculum size is further optimized to 0.2-6% and is further optimized again to 0.5-3%.

Further, a temperature for the shake cultivation treatment in the step (3) ranges from 20 degrees centigrade to 40 degrees centigrade, and the temperature is further optimized to 25-35 degrees centigrade and is further optimized to 26-33 degrees centigrade again; a rotating speed for the shake cultivation treatment ranges from 80 rpm to 250 rpm, and the rotating speed is further optimized to 120-200 rpm, and is further optimized again to 150-180 rpm; a time for the shake cultivation treatment ranges from 48 hours to 216 hours, and the time is further optimized to 60-192 hours and is further optimized again to 72-144 hours.

Further, a rotating speed for the centrifugal treatment in the step (4) ranges from 3000 rpm to 12000 rpm, and the rotating speed is further optimized to 4000-10000 rpm, and is further optimized again to 4500-8000 rpm; a time for the centrifugal treatment ranges from 1-20 minutes, and the time is further optimized to 2-15 minutes and is further optimized again to 3-10 minutes.

Further, the washing in the step (4) includes: washing with a PBS buffer solution is performed first and then washing with normal hexane is performed, so that a lipid-soluble compound left on the cells is removed conveniently.

Further, a concentration of the hydrochloric acid solution in the step (4) ranges from 1 mol/L to 3 mol/L, and a mass volume ratio of the freeze-dried powder to the hydrochloric acid solution ranges from 0.1:2 g/mL to 1:2 g/mL.

Further, the organic solvent in the step (5) includes n-propane, butane, pentane, hexane, heptanes, acetone, trichloromethane, dichloromethane, ethyl ether, methanol and carbon dioxide.

The present invention provides a method for producing special oil OPO by way of microbial fermentation, and the microorganism can be *Rhodococcus opacus* PD630.

Further, the palmitate and oleate include, but not limited to, monoglyceride, diacylglycerol, triacylglycerol, polyglycerol ester, steryl ester, sorbitol ester and the like of palmitic acid and oleic acid.

Further, the carbon source in the optimized culture medium in the step (2) includes an organic carbon source and an inorganic carbon source provided to growth of microorganisms. The carbon source in the optimized culture medium includes, but not limited to, monosaccharides, oligosaccharides and high molecular carbohydrates such as glucose, xylose, fructose, saccharose, dextrin, starch, cellulose, lignin and polysaccharide; various alcohols such as methanol, ethanol, propanol, butanol, pentanol and hexanol; various hydrocarbons such as propane, butane, pentane, hexane, heptanes, octane, nonane, decane, undecane, dodecane, tridecane, tetradecane, pentadecane, cetane, heptadecane, octodecane, nonadecane and eicosane; various fatty acids such as octanoic acid, capric acid, lauric acid, myristic acid, palmitic acid, stearic acid, oleic acid and linoleic acid; and various oils such as peanut oil, soybean soil, repeseed oil, corn oil, palm oil, sunflower seed oil, sesame oil, peony seed oil, rice oil, camellia oil, olive oil, coconut oil, linseed oil and algal oil.

Further, the optimized culture medium in the step (2) includes a carbon source, a nitrogen source, a phosphate, an inorganic salt and water, herein a ratio of amount of carbon substance to nitrogen substance is greater than or equal to 10, and the ratio is further optimized to be greater than or equal to 20 and is further optimized again to be greater than or equal to 30.

Compared with the prior art, the present invention has the following advantages and effects.

The method for producing special oil OPO by way of microbial fermentation provided by the present invention is a brand new technology by adopting a microbial fermentation technique; and the method is simple in process and low in cost, and OPO grows in cells and is safer and healthier.

DETAILED DESCRIPTION OF EXEMPLARY EMBODIMENTS

Figure 1:
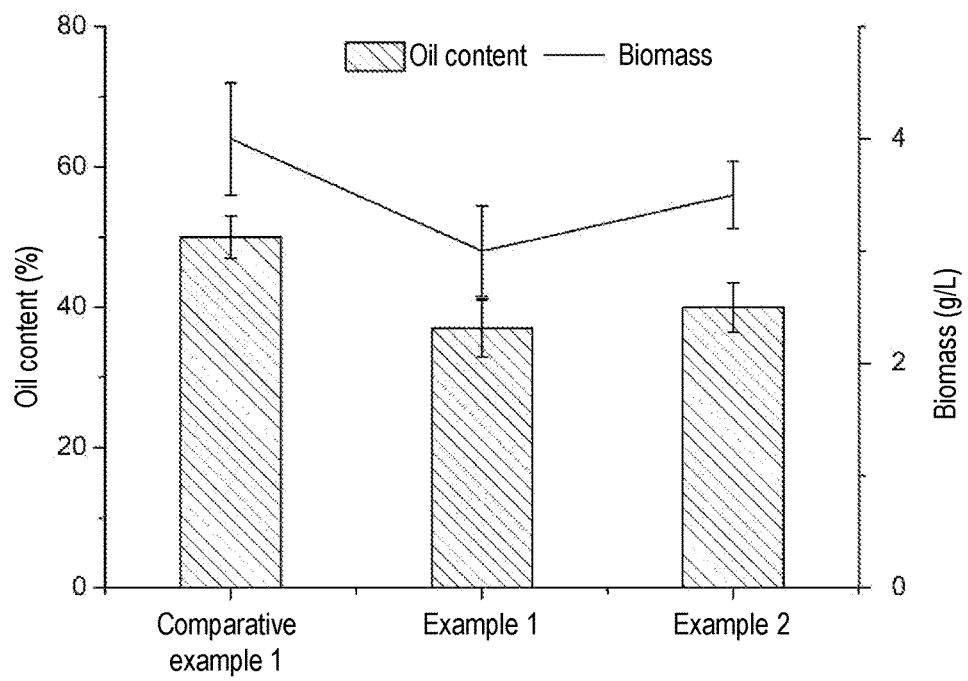
FIG. 1 is a histogram of biomass and oil contents measured in Example 1, Example 2 and Comparative Example 1.

Further description of specific embodiments of the present invention in detail will be made below in combination with drawings and examples, but implementation and protection of the present invention are not limited thereto. It should be noted that processes that are not described in detail particularly below are realized or understood by those skilled in the field with reference to prior art. The used reagents or instruments not indicated by manufacturers are conventional products which can be purchased in the market.

Experimental Method (1) Culture Activation

Rhodococcus is inoculated into an LB culture medium, and cultured for 24 hours at 160 rpm at 30° C., and a culture is activated. The activated culture is a primary fermented culture.

(2) Preparation of an MSM Culture Medium

The culture medium is prepared with reference to Table 1 below (Table 1 is a component table of the MSM culture medium). For example, a volume of the culture medium is 1 liter.

TABLE 1

|  | Unit | Mass/L |
|---|---|---|
| Glucose | g | 24 |
| $KH_2PO_4$ | g | 1.5 |
| $Na_2HPO_4 \cdot 12H_2O$ | g | 9 |
| $NH_4Cl$ | g | 1.0 |
| $MgSO_4 \cdot 7H_2O$ | g | 0.5 |
| $CaCl_2 \cdot 2H_2O$ | mg | 20 |
| $Na_2MoO_4 \cdot 2H_2O$ | mg | 2 |
| $FeNaEDTA \cdot 3H_2O$ | mg | 5 |
| $CoCl_2 \cdot 6H_2O$ | mg | 0.2 |
| $ZnSO_4 \cdot 7H_2O$ | mg | 0.1 |
| $MnCl_2 \cdot 4H_2O$ | mg | 0.05 |
| $H_3BO_3$ | mg | 0.3 |
| $CuCl_2 \cdot 2H_2O$ | mg | 0.1 |
| $NiCl_2 \cdot 6H_2O$ | mg | 0.2 |

(3) Cultivation of Culture

The MSM culture medium is prepared with reference to Table 1, and the obtained MSM culture medium is subject to sterilizing treatment at 121° C., where the time for sterilizing treatment for 12 minutes; the culture medium is subpackaged to a 250 mL conical flask, and the culture activated in the step (1) is inoculated to the 250 ml conical flask, where an inoculum size is 1% (v/v); cultivation is performed for 4 days in a table, where the temperature is 30° C. and the rotating speed is 160 rpm; and then the culture is collected by a centrifugal method, where the centrifugal rotating speed is 6000 rpm and the centrifugal time is 2 minutes, thereby obtaining a cell precipitate.

(4) Biomass Test Method

The cell precipitate in the step (3) is washed with a 0.1% (w/w) PBS buffer solution for three times, residual culture medium on the cell precipitate is removed, and the cell precipitate is washed with normal hexane for three times to remove the liposoluble compound in the culture medium; and then the cell precipitate is freeze-dried to obtain a freeze-dried cell powder, the powder is weighed and the biomass is calculated.

(5) Oil Content Detection Method 0.1 g of the freeze-dried cell powder in the step (4) is weighed, 2 mL of 3 mol/L HCl solution is added, the freeze-dried cell powder and the HCl solution are mixed uniformly, water bathing is performed for 30 minutes at 80° C., then 2 mL of trichloromethane is added for extraction for three times, three extraction liquids are combined, trichloromethane in the extraction liquid is blow-dried with nitrogen to obtain an oil mixture, and the oil content is weighed and calculated.

(6) Total Fatty Acid Composition Determination (National Food Safety Standard GB 5009.168-2016)

0.02 g of the oil mixture in the step (5) is taken, the oil mixture is added into 2 ml normal hexane to be dissolved, the oil mixture is stirred uniformly, 2 mL of a methanol solution with a concentration of 0.5 mol/L sodium hydroxide is then added, water bathing is performed at 60° C. for 20 minutes to complete a methyl esterification reaction, a supernate (normal hexane) is taken, and composition of the fatty acid is analyzed by a gas chromatographic method. Conditions of the gas chromatographic method are as follows: a chromatographic column is HP-5, a temperature of a column oven is 180° C., a temperature at a sample feeding port is 190° C., and a temperature of a detector is 270° C. A result graph is obtained, and the type of fatty acid is determined according to a retention time of a peak.

(7) Sn-2 Fatty Acid Composition Determination (National Food Safety Standard GB 5009.168-2016)

The oil mixture is developed by using a thin layer chromatography plate, and an unfolder is composed of normal hexane, absolute ether and glacial acetic acid at a ratio of 70:30:2 (v/v/v). Triacylglycerol is scraped and is extracted with normal hexane for three times to obtain pure triacylglycerol. Triacylglycerol is put in a 15 mL centrifuge tube, tri-HCl hydrochloric acid, sodium cholate, $CaCl_2$ and lipase are added, water bathing is then performed for 1 min, then 1 mL of 6 mol/L hydrochloric acid solution is added to deactivate the lipase, and ethyl ether is added to extract a lipid. An ethyl ether extraction matter is developed on the thin layer chromatography plate, and monoglyceride is scraped partially for methyl esterification, and gas chromatography is performed to analyze composition of the fatty acid.

Comparative Example 1

(1) Culture activation

The microorganism (Rhodococcus opacus PD630) was inoculated to an activating culture medium (LB culture medium), shake cultivation treatment was performed, a temperature for shake cultivation treatment was 30 degrees centigrade, a rotating speed for shake cultivation treatment was 160 rpm, and a time for shake cultivation treatment was 24 hours, thereby, an activated culture was obtained;

(2) Preparation of an MSM culture medium

The MSM culture medium was prepared according to a formula of Table 1, and sterilizing treatment (high-temperature and high-pressure sterilization) was performed to obtain the MSM culture medium;

(3) The activated culture in the step (1) was inoculated into the optimized culture medium in the step (2) for shake cultivation treatment, where the inoculum size was 1% (v/v), where a temperature for shake cultivation treatment was 30 degrees centigrade, a time for shake cultivation treatment was 96 hours and a rotating speed for shake cultivation treatment was 160 rpm, thereby obtaining a culture solution;

(4) The culture solution in the step (3) was subject to centrifugal treatment, where a speed of centrifugal treatment was 6000 rpm and a time for centrifugal treatment was 2 minutes, a cell precipitate was taken and washed with a 0.1% (w/w) PBS buffer solution for three times, residual culture medium on the cell precipitate was removed, and the cell precipitate was washed with normal hexane to remove the liposoluble compound in the culture medium; and then the cell precipitate was freeze-dried to obtain a freeze-dried cell powder, the powder was weighed and the biomass was calculated;

(5) 0.1 g of the freeze-dried cell powder in the step (4) was weighed, 2 mL of 3 mol/L HCl solution was added, the freeze-dried cell powder and the HCl solution were mixed uniformly, water bathing was performed for 30 minutes at 80° C., then 2 mL of trichloromethane was added for extraction for three times, three extraction liquids were combined, trichloromethane in the extraction liquid was blow-dried with nitrogen to obtain an oil mixture, and the oil content was weighed and calculated; 0.02 g of the oil mixture was taken and added into 2 ml normal hexane to be dissolved, the oil mixture was stirred uniformly, 2 mL of a methanol solution with a concentration of 0.5 mol/L sodium hydroxide was then added, water bathing was performed at 60° C. for 20 minutes to complete a methyl esterification reaction, a supernate (normal hexane) was taken, and composition of the fatty acid was analyzed by a gas chromatographic method; and (6) Composition of Sn-2 fatty acid of the oil mixture was tested (determined according to National Food Safety Standard GB 5009.168-2016).

Comparative Example 2

Two oils were selected, palm stearin (HPO with high content of palmitic acid) and sunflower seed oil (HOSFO) with high oleic acid, the two oils were blended at a proportion of 1:2 (mass ratio), then ester exchange was performed, and compositions of the total fatty acid and sn-2 fatty acid composition were determined (determined according to National Food Safety Standard GB 5009.168-2016).

Example 1

A method for producing special oil OPO by way of microbial fermentation includes the following steps:

(1) Culture activation

The microorganism (*Rhodococcus opacus* PD630) was inoculated to an activating culture medium (LB culture medium), shake cultivation treatment was performed, a temperature for shake cultivation treatment was 30 degrees centigrade, a rotating speed for shake cultivation treatment was 160 rpm, and a time for shake cultivation treatment was 24 hours, thereby, an activated culture was obtained;

(2) Preparation of an optimized culture medium

An MSM culture medium was prepared according to a formula of Table 1, and in the preparation process, 0.8 g of ethyl oleate and 0.4 g of ethyl palmitate (a mass ratio of ethyl oleate to ethyl palmitate was 2:1), were added into a culture medium and mixed uniformly, and were subject to sterilizing treatment (high-temperature and high-pressure sterilization), thereby obtaining an optimized culture medium;

(3) The activated culture in the step (1) was inoculated into the optimized culture medium in the step (2) for shake cultivation treatment, where the inoculum size was 1% (v/v), where a temperature for shake cultivation treatment was 30 degrees centigrade, a time for shake cultivation treatment was 96 hours and a rotating speed for shake cultivation treatment was 160 rpm, thereby obtaining a culture solution;

(4) The culture solution in the step (3) was subject to centrifugal treatment, where a speed of centrifugal treatment was 6000 rpm and a time for centrifugal treatment was 5 minutes, a cell precipitate was obtained, and washed with a 0.1% (w/w) PBS buffer solution for three times, residual culture medium on the cell precipitate was removed, and the cell precipitate was washed with normal hexane to remove the liposoluble compound in the culture medium; and then the cell precipitate was freeze-dried to obtain a freeze-dried cell powder, the powder was weighed and the biomass was calculated;

(5) 0.1 g of the freeze-dried cell powder in the step (4) was weighed, 2 mL of 3 mol/L HCl solution was added, the freeze-dried cell powder and the HCl solution were mixed uniformly, water bathing was performed for 30 minutes at 80° C., then 2 mL of trichloromethane was added for extraction for three times, three extraction liquids were combined, trichloromethane in the extraction liquid was blow-dried with nitrogen to obtain an oil mixture (the oil mixture contains the special oil OPO); and (6) Compositions of the total fatty acid composition, the Sn-2 fatty acid composition and the oil mixture of the oil mixture in the step (5) were tested (determined according to National Food Safety Standard GB 5009.168-2016).

Example 2

A method for producing special oil OPO by way of microbial fermentation includes the following steps:

(1) Culture activation

The microorganism (*Rhodococcus opacus* PD630) was inoculated to an activating culture medium (LB culture medium), shake cultivation treatment was performed, a temperature for shake cultivation treatment was 30 degrees centigrade, a rotating speed for shake cultivation treatment was 160 rpm, and a time for shake cultivation treatment was 24 hours, thereby, an activated culture was obtained;

(2) Preparation of an optimized culture medium

An MSM culture medium was prepared according to a formula of Table 1, and in the preparation process, 0.4 g of HPO and 0.8 g of HOSFO (a mass ratio of HPO to HOSFO was 1:2), were added into a culture medium and mixed uniformly, and were subject to sterilizing treatment (high-temperature and high-pressure sterilization), thereby obtaining an optimized culture medium;

(3) The activated culture in the step (1) was inoculated into the optimized culture medium in the step (2) for shake cultivation treatment, where the inoculum size was 1% (v/v), where a temperature for shake cultivation treatment was 30 degrees centigrade, a time for shake cultivation treatment was 96 hours and a rotating speed for shake cultivation treatment was 160 rpm, thereby obtaining a culture solution;

(4) The culture solution in the step (3) was subject to centrifugal treatment, where a speed of centrifugal treatment was 6000 rpm and a time for centrifugal treatment was 5 minutes, a precipitate was taken to obtain a cell precipitate, the cell precipitate was washed with a 0.1% (w/w) PBS buffer solution for three times, residual culture medium on the cell precipitate was removed, and the cell precipitate was washed with normal hexane to remove the liposoluble compound in the culture medium; and then the cell precipitate was freeze-dried to obtain a freeze-dried cell powder, the powder was weighed and the biomass was calculated;

(5) 0.1 g of the freeze-dried cell powder in the step (4) was weighed, 2 mL of 3 mol/L HCl solution was added, the freeze-dried cell powder and the HCl solution were mixed uniformly, water bathing was performed for 30 minutes at 80° C., then 2 mL of trichloromethane was added for extraction for three times, three extraction liquids were combined, trichloromethane in the extraction liquid was blow-dried with nitrogen to obtain an oil mixture (the oil mixture contains the special oil OPO);

(6) Compositions of the full-sample fatty acid, the Sn-2 fatty acid and the oil mixture of the oil mixture in the step (5) were tested (determined according to National Food Safety Standard GB 5009.168-2016).

Example 3

A method for producing special oil OPO by way of microbial fermentation includes the following steps:
(1) Culture activation The microorganism (*Rhodococcus opacus* PD630) was inoculated to an activating culture medium (LB culture medium), shake cultivation treatment was performed, a temperature for shake cultivation treatment was 20 degrees centigrade, a rotating speed for shake cultivation treatment was 250 rpm, and a time for shake cultivation treatment was 12 hours, thereby, an activated culture was obtained;

(2) Preparation of an optimized culture medium

An MSM culture medium was prepared according to a formula of Table 1, and in the preparation process, 1.6 g of ethyl oleate and 0.8 g of ethyl palmitate (a mass ratio of ethyl oleate to ethyl palmitate was 2:1), were added into a culture medium and mixed uniformly, and were subject to sterilizing treatment (high-temperature and high-pressure sterilization), thereby obtaining an optimized culture medium;

(3) The activated culture in the step (1) was inoculated into the optimized culture medium in the step (2) for shake cultivation treatment, where the inoculum size was 10% (v/v), where a temperature for shake cultivation treatment was 40 degrees centigrade, a time for shake cultivation treatment was 216 hours and a rotating speed for shake cultivation treatment was 80 rpm, thereby obtaining a culture solution;

(4) The culture solution in the step (3) was subject to centrifugal treatment, where a speed of centrifugal treatment was 12000 rpm and a time for centrifugal treatment was 1 minute, a cell precipitate was obtained and washed with a 0.1% (w/w) PBS buffer solution for three times, residual culture medium on the cell precipitate was removed, and the cell precipitate was washed with normal hexane to remove the liposoluble compound in the culture medium; and then the cell precipitate was freeze-dried to obtain a freeze-dried cell powder, the powder was weighed and the biomass was calculated;

(5) 0.5 g of the freeze-dried cell powder in the step (4) was weighed, 2 mL of 1 mol/L HCl solution is added, the freeze-dried cell powder and the HCl solution were mixed uniformly, water bathing was performed for 30 minutes at 80° C., then 2 mL of trichloromethane was added for extraction for three times, three extraction liquids were combined, trichloromethane in the extraction liquid was blow-dried with nitrogen to obtain an oil mixture (the oil mixture contains the special oil OPO);

(6) Compositions of the total fatty acid composition, the Sn-2 fatty acid composition and the oil mixture of the oil mixture in the step (5) were tested (determined according to National Food Safety Standard GB 5009.168-2016).

Example 4

A method for producing special oil OPO by way of microbial fermentation includes the following steps:
(1) Culture activation The microorganism (*Rhodococcus opacus* PD630) was inoculated to an activating culture medium (LB culture medium), shake cultivation treatment was performed, a temperature for shake cultivation treatment was 40 degrees centigrade, a rotating speed for shake cultivation treatment was 80 rpm, and a time for shake cultivation treatment was 60 hours, thereby, an activated culture is obtained;

(2) Preparation of an optimized culture medium

An MSM culture medium was prepared according to a formula of Table 1, and in the preparation process, 0.8 g of HPO and 1.6 g of HOSFO (a mass ratio of HPO to HOSFO was 1:2), were added into a culture medium and mixed uniformly, and were subject to sterilizing treatment (high-temperature and high-pressure sterilization), thereby obtaining an optimized culture medium;

(3) The activated culture in the step (1) was inoculated into the optimized culture medium in the step (2) for shake cultivation treatment, where the inoculum size was 0.1% (v/v), where a temperature for shake cultivation treatment was 20 degrees centigrade, a time for shake cultivation treatment was 48 hours and a rotating speed for shake cultivation treatment was 250 rpm, thereby obtaining a culture solution;

(4) The culture solution in the step (3) was subject to centrifugal treatment, where a speed of centrifugal treatment was 3000 rpm and a time for centrifugal treatment was 20 minutes, a cell precipitate was obtained and washed with a 0.1% (w/w) PBS buffer solution for three times, residual culture medium on the cell precipitate was removed, and the cell precipitate was washed with normal hexane to remove the liposoluble compound in the culture medium; and then the cell precipitate was freeze-dried to obtain a freeze-dried cell powder, the powder was weighed and the biomass was calculated;

(5) 2 g of the freeze-dried cell powder in the step (4) was weighed, 1 mL of 2 mol/L HCl solution was added, the freeze-dried cell powder and the HCl solution were mixed uniformly, water bathing was performed for 30 minutes at 80° C., then 2 mL of trichloromethane was added for extraction for three times, three extraction liquids were combined, trichloromethane in the extraction liquid was blow-dried with nitrogen to obtain an oil mixture (the oil mixture contains the special oil OPO); and (6) Compositions of the total fatty acid composition, the Sn-2 fatty acid composition and the oil mixture of the oil mixture in the step (5) were tested (determined according to National Food Safety Standard GB 5009.168-2016).

Result Analysis

A test result is seen in Table 2, FIG. 1, FIG. 2, FIG. 3, and FIG. 4 below, and Table 2 below is a data table (%) of composition of main fatty acids of an oil sample.

TABLE 2

| Fatty acid | Example 1 | | Example 2 | | Comparative Example 1 | | Comparative Example 2 | |
| --- | --- | --- | --- | --- | --- | --- | --- | --- |
| | Total | SN-2 | Total | SN-2 | Total | SN-2 | Total | SN-2 |
| C14:0 | 2.39 | 5.40 | 2.40 | 4.96 | 1.77 | 11.1 | 0.26 | 0.31 |
| C16:0 | 29.83 | 74.54 | 28.27 | 65.67 | 28.94 | 59.0 | 30.41 | 33.72 |
| C16:1 | 4.07 | 4.58 | 5.48 | 12.38 | 7.01 | 0.01 | | |
| C18:0 | | 0.95 | 1.33 | 2.02 | 5.53 | 2.1 | 3.21 | 3.18 |
| C18:1 | 55.78 | 5.69 | 60.70 | 11.46 | 20.62 | 0.5 | 61.49 | 59.25 |
| C18:2 | 3.01 | 0.68 | 1.81 | 1.06 | 1.49 | | 4.04 | 3.55 |

It can be known from Table 2 that the content of oleic acid in the composition of the fatty acids of oil is relatively low, and a proportion of palmitic acid to oleic acid is 1:0.7. The total fatty acid and the sn-2 fatty acid composition in the comparative example 2 are consistent, which means that the fatty acids are completely distributed at random on a glycerol backbone. In the Example 1, the proportion of palmitic acid to oleic acid in the composition of the total fatty acid composition is 1:1.87, and the content of palmitic acid in the sn-2 fatty acid composition is 74.54%, which means that triacylglycerol is OPO. In Example 2, the proportion of palmitic acid to oleic acid in the composition of the total fatty acid composition is 1:2.15, and the content of palmitic acid in the sn-2 fatty acid composition is 65.67%, which means that triacylglycerol is OPO.

Figure 2:
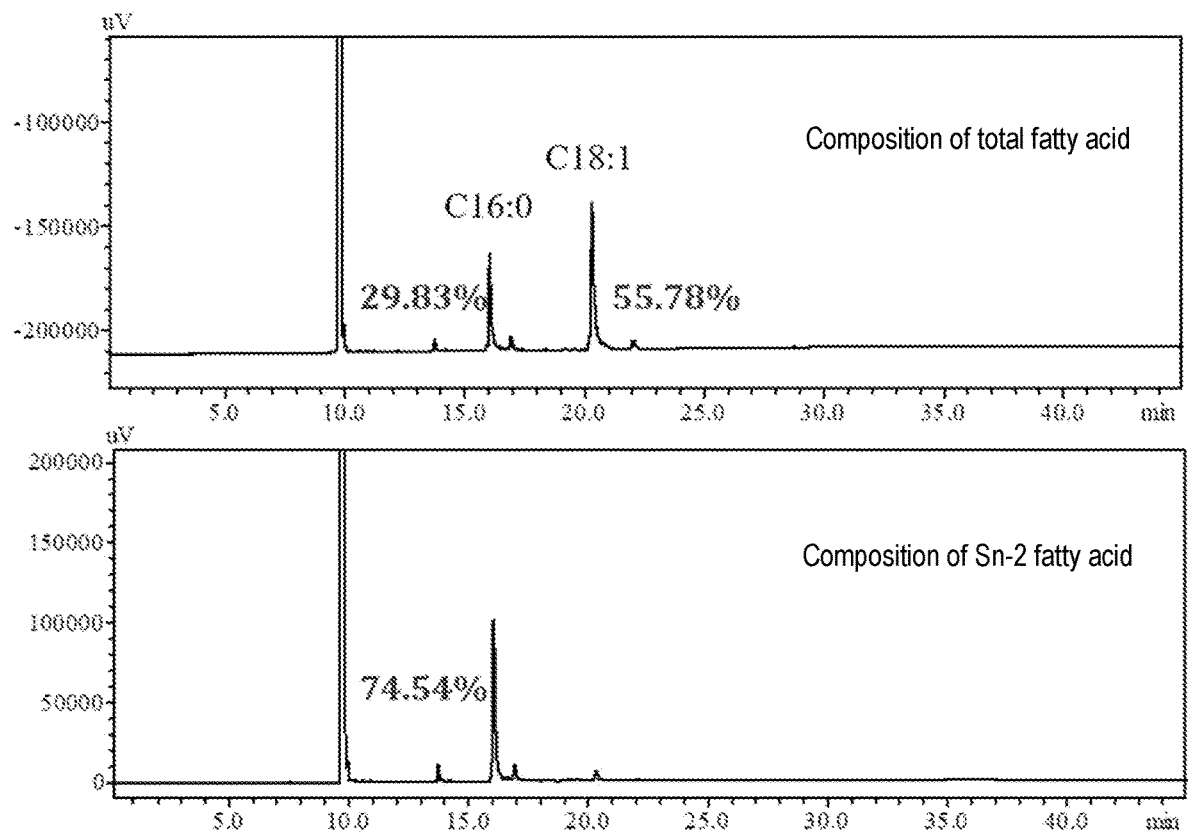
FIG. 2 is a gas chromatogram composed of fatty acid of oil in Example 1.
Figure 3:
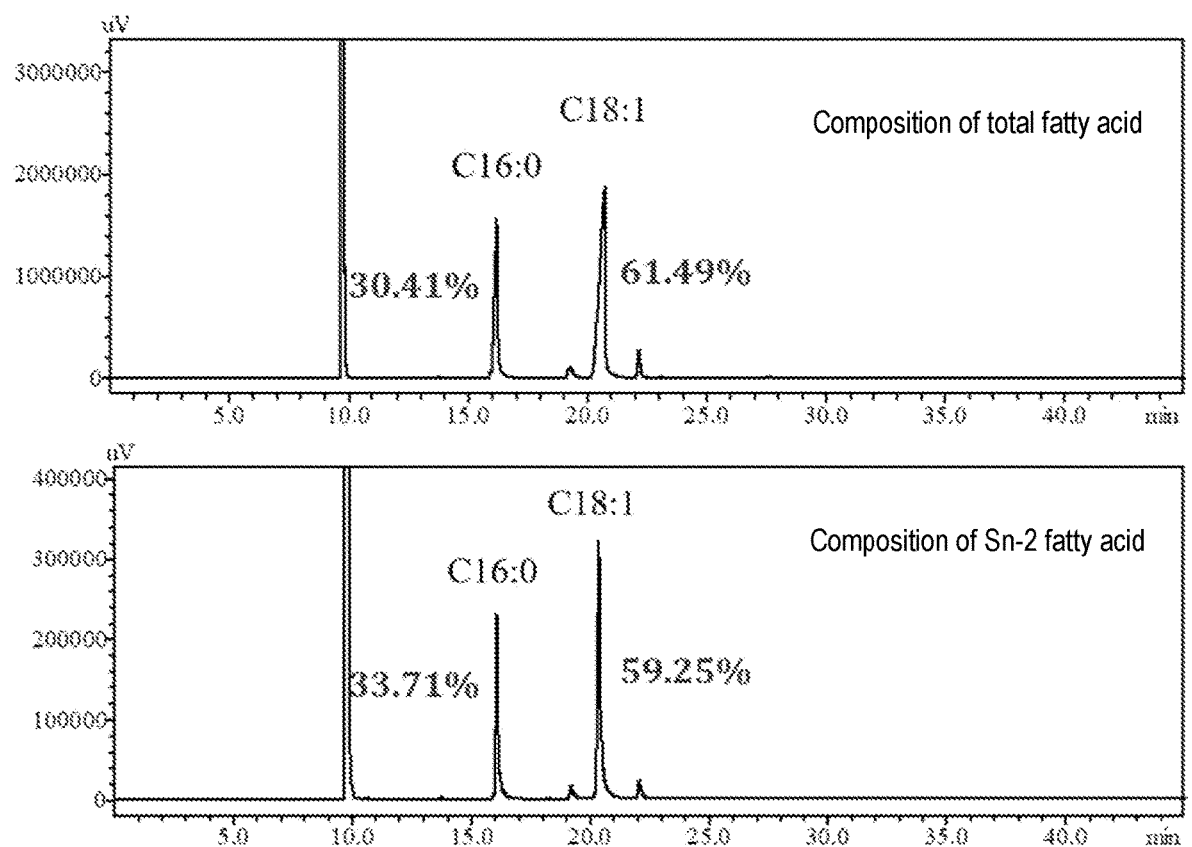
FIG. 3 is a gas chromatogram composed of fatty acid of oil in Comparative Example 2.
Figure 4:
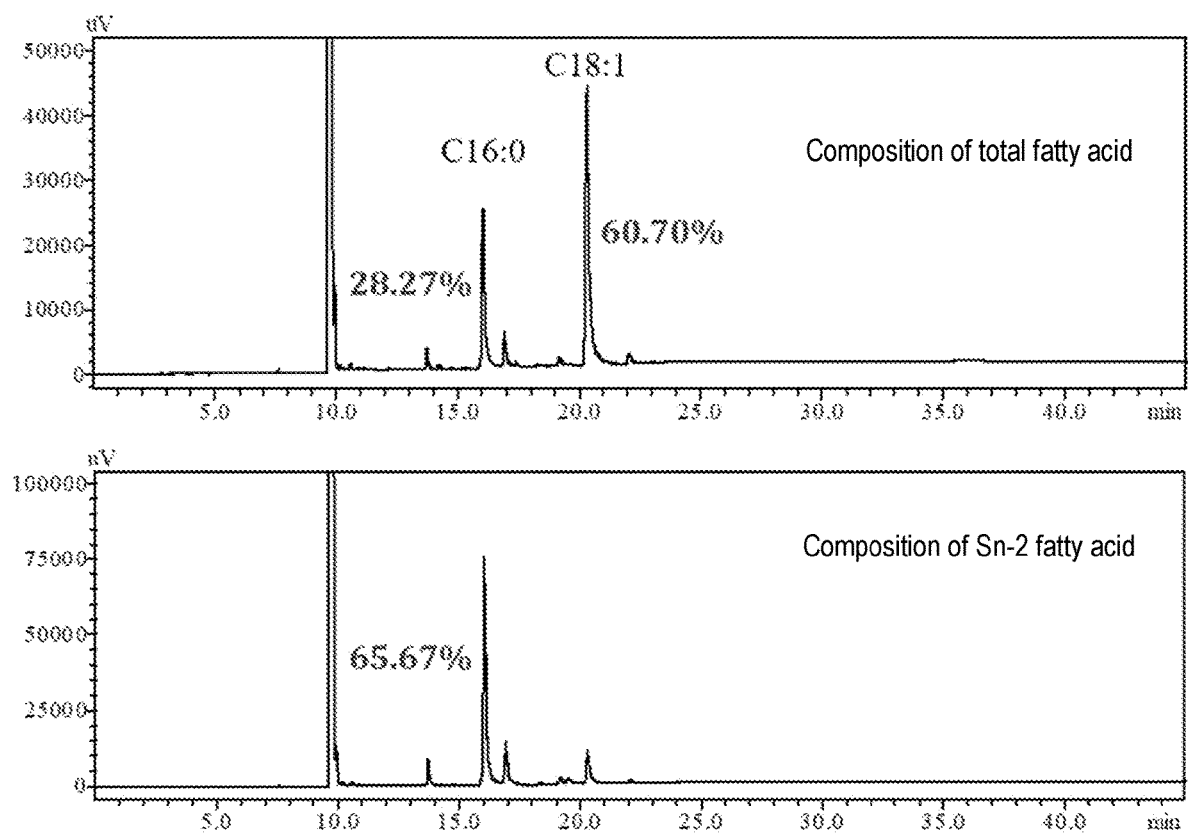
FIG. 4 is a gas chromatogram composed of fatty acid of oil in Example 2.

Effects of Examples 3 and 4 are similar to that of Example 1, which can refer to FIG. 1, FIG. 2 and FIG. 4, and Table 2.

The above embodiments are merely preferred embodiments of the present invention and are merely used for explaining the present invention rather than limiting the present invention. Variations, substitutions and modifications made by those skilled in the field shall fall within the scope of protection of the present invention without departing from the spirit of the present invention.

What is claimed is:

1. A method for producing 1,3-dioleic acid-2-palmitic acid triglyceride (OPO) oil by way of microbial fermentation, comprising the following steps:
    (1) inoculating *Rhodococcus opacus* PD630 to an activating culture medium, and carrying out a shake cultivation treatment to obtain an activated culture;
    (2) adding an organic matter into a minimal medium, uniformly mixing, and carrying out a sterilizing treatment to obtain an optimized culture medium;
    (3) inoculating the activated culture in the step (1) into the optimized culture medium in the step (2) and carrying out the shake cultivation treatment to obtain a culture solution;
    (4) carrying out a centrifugal treatment on the culture solution in the step (3), taking a precipitate, washing the precipitate and freezing and drying the precipitate to obtain a freeze-dried powder, adding a hydrochloric acid solution, and uniformly mixing to obtain a mixture; and
    (5) adding an organic solvent into the mixture in the step (4), carrying out an extraction treatment, and removing the organic solvent to obtain the 1,3-dioleic acid-2-palmitic acid triglyceride (OPO) oil, wherein the organic matter in the step (2) comprises palmitic acid, oleic acid, palmitate, oleate, cetane, octodecane, palm oil, and a fractionated product of palm oil, and
    wherein the organic solvent in the step (5) comprises n-propane, butane, pentane, hexane, heptanes, acetone, trichloromethane, dichloromethane, ethyl ether, methanol, and carbon dioxide.

2. The method for producing 1,3-dioleic acid-2-palmitic acid triglyceride (OPO) oil by way of microbial fermentation according to claim 1, wherein the activating culture medium comprises a bouillon culture-medium and an LB culture medium.

3. The method for producing 1,3-dioleic acid-2-palmitic acid triglyceride (OPO) oil by way of microbial fermentation according to claim 1, wherein in the step (1), a temperature for the shake cultivation treatment ranges from 20 degrees centigrade to 40 degrees centigrade, a rotating speed for the shake cultivation treatment ranges from 80 rpm to 250 rpm, and a time for the shake cultivation treatment ranges from 12 hours to 60 hours.

4. The method for producing 1,3-dioleic acid-2-palmitic acid triglyceride (OPO) oil by way of microbial fermentation according to claim 1, wherein an additive amount of the organic matter is 0.1-10% of the minimal medium by mass, and the minimal medium comprises an MSM culture medium.

5. The method for producing 1,3-dioleic acid-2-palmitic acid triglyceride (OPO) oil by way of microbial fermentation according to claim 1, wherein the sterilizing treatment in the step (2) comprises high-temperature and high-pressure sterilization, and medium and low-pressure sterilization.

6. The method for producing 1,3-dioleic acid-2-palmitic acid triglyceride (OPO) oil by way of microbial fermentation according to claim 1, wherein an inoculum size of the inoculating in the step (3) is 0.1-10% of the optimized culture medium by volume.

7. The method for producing 1,3-dioleic acid-2-palmitic acid triglyceride (OPO) oil by way of microbial fermentation according to claim 1, wherein in the step (3), a temperature for the shake cultivation treatment ranges from 20 degrees centigrade to 40 degrees centigrade, a rotating speed for the shake cultivation treatment ranges from 80 rpm to 250 rpm, and a time for the shake cultivation treatment ranges from 48 hours to 216 hours.

8. The method for producing 1,3-dioleic acid-2-palmitic acid triglyceride (OPO) oil by way of microbial fermentation according to claim 1, wherein in the step (4), a rotating speed for the centrifugal treatment ranges from 3000 rpm to 12000 rpm, and a time for the centrifugal treatment ranges from 1 min to 20 min.

9. The method for producing 1,3-dioleic acid-2-palmitic acid triglyceride (OPO) oil by way of microbial fermentation according to claim 1, wherein a concentration of the hydrochloric acid solution in the step (4) ranges from 1 mol/L to 3 mol/L, and a mass volume ratio of the freeze-dried powder to the hydrochloric acid solution ranges from 0.1:2 g/mL to 1:2 g/mL.

* * * * *